United States Patent [19]

Le Febre

[11] Patent Number: 5,692,078
[45] Date of Patent: Nov. 25, 1997

[54] HIGH TEMPERATURE CONNECTOR FOR FUSED SILICA CAPILLARY BODY

[75] Inventor: David A. Le Febre, Camino, Calif.

[73] Assignee: UOP, Des Plaines, Ill.

[21] Appl. No.: 545,080

[22] Filed: Oct. 19, 1995

[51] Int. Cl.$^6$ .................. G02B 6/00; G02B 6/36
[52] U.S. Cl. ........................................... 385/53
[58] Field of Search .................... 385/53, 55, 56, 385/60, 62, 66, 76, 78, 80, 81

[56] References Cited

U.S. PATENT DOCUMENTS

| | | | |
|---|---|---|---|
| 4,458,983 | 7/1984 | Roberts | 385/62 X |
| 4,668,044 | 5/1987 | D'Auria et al. | 385/55 X |
| 4,883,336 | 11/1989 | Bock et al. | 385/53 X |
| 4,891,640 | 1/1990 | Ip | 385/53 |
| 4,984,867 | 1/1991 | Giovanna | 385/56 |
| 5,113,463 | 5/1992 | Nodari | 385/56 X |
| 5,239,602 | 8/1993 | Hunsberger et al. | 385/62 |
| 5,276,750 | 1/1994 | Manning | 385/56 |

*Primary Examiner*—Akm E. Ullah
*Attorney, Agent, or Firm*—Thomas K. McBride; John G. Tolomei

[57] ABSTRACT

A connector for joining small diameter fused silica tubing or fibers to similar or dissimilar materials that use an included taper angle of from 20° to 40° on a conical tapered section of a fused silica body to provide a reliable high temperature connection. The taper angle provides a compressive loading on the fused silica. The connection avoids tensile loads on the small diameter section of the fused silica. The tensile loads can cause cracking of the silica. The connection is lightweight and provides a tight seal at temperatures of 600° C. or more. This connector is particularly suited for connecting capillary tubing to metallic tubing at high temperatures.

24 Claims, 4 Drawing Sheets

HIGH TEMPERATURE CONNECTOR FOR FUSED SILICA CAPILLARY BODY

FIELD OF THE INVENTION

The present invention relates generally to fused silica tubing and fibers for gas chromatography and optical wave communication. More specifically this invention relates to connectors for fused silica tubing and solid fused silica optical fibers.

BACKGROUND OF THE INVENTION

Fused silica has found wide spread use as a capillary tubing material for gas chromatography applications and in glass on glass optical wave guide fibers. Practical arrangements for connecting fused silica capillaries and fibers to detection devices has presented a number of challenges in many applications. The free diameters of tubing and fiber structures and the low tensile strength of fused silica materials makes the arrangement of connectors for the capillary tubes and fibers especially difficult.

Connecting fused silica capillary tubes to analytical equipment for detection and analysis provided an unexpected challenge. The small diameter capillary tubing comprising the fused silica can withstand only very low tensile loads and has a much lower coefficient of thermal expansion than the metallic materials type used to retain sealing elements for connections. These characteristics of the fused silica material limit the type and performance of connectors that can be used. The general approach of the prior art applies radial type fittings using O-rings or other relatively bulky seals to the ends of fused silica tubing. Physical size limitations of the capillary tubing are overcome to some extent by the use of a connector body to provide a larger diameter connector body or interface tube to which connections may be made. Whether using a connector body or attempting to made direct connections to a silica tube, known radial type connectors have several disadvantages. The O-ring arrangements add substantial bulk to the end of the capillary tubing or the connector body. The bulk of the connections can lead to fatigue or stress failures at the connector. Most O-ring arrangements also leave a gap between the bores of the tubing joined across the connector. Such gaps serve as dead volumes that interfere with accurate fluid transmission and detection from the capillary tube. Another serious operational problem is posed by high temperature operation which causes the O-rings associated with the radial firings to leak after several temperature cycles or to require repeated tightening. The need to continually tighten connectors on fragile connector bodies or capillary tubes interferes with high temperature operations and can again, lead to brittle failure of the silica connector structures.

Investigation of face type seals was undertaken to eliminate the problems and limitations created by radial type seals. However, the low tensile strength properties of the fused silica combined with its low coefficient of expansion created substantial difficulties in discovering an acceptable face seal connector arrangement. Suitable face seal arrangements require a highly leak resistant seal that must prevent leakage under vacuum and pressure loading conditions. At the same time, sealing pressure applied to the face of the fused silica must be done without developing tensile stresses that will cause fracturing or breakage of the fused silica face. It is also desired that the connector provide an effective seal with repeated temperature cycles of 600° C. or more.

Many of the same problems associated with fused silica capillary tubes also arise when sealing detection ends for fibers of fused silica in high temperature or high pressure environments. Examples of such an application is the detection of emission spectra from hydrocarbon detonation in the cylinder walls of combustion chambers or the inside of furnaces. Both of these applications impose high temperatures on the end of the fiber that detects the spectra and, in the case of the cylinder wall, high pressures are imposed as well. These conditions have made provision of a reliable seal at the detection end of the fiber difficult to achieve.

SUMMARY OF THE INVENTION

By controlling the taper angle on the end of the fused silica connector and the mating angle in the alignment block, it has been found that a connector having a fused silica body can provide a suitable seal for vacuum operation or high pressure operation at high temperature conditions that withstands repeated temperature cycles of over 600° C. This invention is a connector arrangement for fused silica tubing and optical transmission fibers that seals the connections for operations at vacuum or pressure conditions with repeated temperature cycles of up to 600° C. or more. The connector is light weight and for typical capillary tubing and fibers arrangements weighs less than 15 grams. The arrangement consists of a tapered end on a fused silica body having a included tapered surface. The slope of the tapered surface can vary within a range of about 10° to 20° along the primary axis of the fused silica body. Therefore for a conical taper the total include angle will be between 20°–40°. The fused silica body may be an independent member attached to capillary tube or filament or an integral part of a fused silica capillary tube or filament. An alignment block having substantially the same taper angle receives the tapered end of the fused silica body and maintains a compressive loading on the end of the fused silica body. For the purposes of this description substantially the same taper angle means that the slope of the surfaces at the point of contact will have an angular variation of less than 0.5 degrees, preferably less than 0.3 degrees and more preferably less than 0.1 degrees. The alignment block can be an integral part of a structure such as a cylinder wall that receives the silica body or a separate component of a connection arrangement. The compression load provided by the alignment block eliminates tensile stress on the end of the fused silica tube and prevents fractures. Bolts or other tensioning members urge the alignment block toward the fused silica tube with sufficient force to create the compressive loading on the end of the fused silica. The compressive force provided on the fused silica can be sufficient to create a seal between the tapered surfaces of the alignment block and the end of the fused silica.

The bolts or other tensioning members can also provide an additional or alternate seal between the end of the fused silica and an additional contact face. The additional contact face is most suitably located on the convergent end of the fused silica body and cooperates with a corresponding contact face on an additional sealing element. In the case of the fused silica tubing, the additional contact face can comprise the transverse profile of an additional tubing element. In a preferred arrangement the alignment block can provide a bore for aligning the opposing face seal for contact with the face of a fused silica body that is bonded to fused silica tubing. Spring elements may also serve as biasing members to control the pressure generated on the tapered faces as well as the contact face of additional sealing surfaces.

Accordingly, in a broad embodiment this invention is a connector arrangement for making connections to fused silica tubing or fibers. The connector includes a fused silica body defining a convergent tapered surface formed on the outside of the distil end of the body. The convergent tapered surface has an included angle of from 20°–40°. An alignment body defines a bore which forms a divergent surface tapered at substantially the same included angle as the taper on the end of the fused silica body. The alignment body receives the distal end of the silica body. Means are also provided for securing the fused silica body into the alignment block and urging the convergent and divergent tapered surfaces into contact.

In more limited embodiment this invention is a connector arrangement for making connections to fused silica tubing. The connector includes a fused silica body defining a first bore open to a distal end of the body and a convergent tapered surface formed on its outside. The convergent tapered surface has an included angle of from 20°–40°. An alignment body defines another bore which at one end forms a divergent surface tapered at substantially the same included angle as the taper on the end of the fused silica body. The alignment body receives the distal end of the silica body. Means are also provided for securing a conduit to the alignment block, communicating the conduit with the end of the silica body and urging the tapered surfaces of the fused silica body and alignment body into contact.

In a more specific embodiment, this invention is a connector that includes a fused silica body fixed to a capillary tube at a proximate end that defines a first bore communicating with the bore of the capillary tube. The outside end of the silica body forms a truncated conical surface that converges in the direction of the distal end of the silica body. The truncated surface defines a convergent tapered surface having an included angle of from 20°–40°. The silica body also defines a first contact face that surrounds the end of the first bore. An alignment body defines a second bore having one end forming a concave, truncated conical surface. The conical surface has a divergent taper substantially equal to the included angle of the convergent surface on the silica body. A second contact face, located in the second bore, has a surface that contacts the first contact face while defining a central opening. Means are provided for securing a conduit to the alignment block and communicating the conduit with the central opening and urging the divergent and convergent tapered surfaces and the first and second contact faces into contact.

DETAILED DISCLOSURE OF THE INVENTION

This connector arrangement is highly useful for joining connectors to fused silica tubing or fibers. The connector may be used directly on the end of capillary tube or fiber having sufficient size to support the physical components of the connector or may be used with the connector body made in the general form of tubing nipple that serves as an intermediate piece between the capillary tubing or fiber and the other connected member to which the capillary or fiber is attached or secured. The connector arrangement will typically join capillary tubing to metallic tubing and to position optical wave guide fibers in position on solid bodies, but can also be used to join capillary tubing or fibers to additional capillary tubing or fibers. Typical capillary tubing used with this invention will have outer diameters ranging from 250 to 650 μm with capillary bores sizes of from 75 to 530 μm. The core diameter of glass on glass optical wave guides will usually range from 250 to 600 μm.

The usual application of this connection is in a capillary system for gas chromatography. The connector arrangement is first described in the context of its application to fused silica capillary tubing. Those skilled in the art will readily recognize other methods and arrangement to utilize this invention with other configurations of fused silica and the description of this invention in the context of fused silica tubing is not meant to limit this invention to the particular application.

Figure 1:
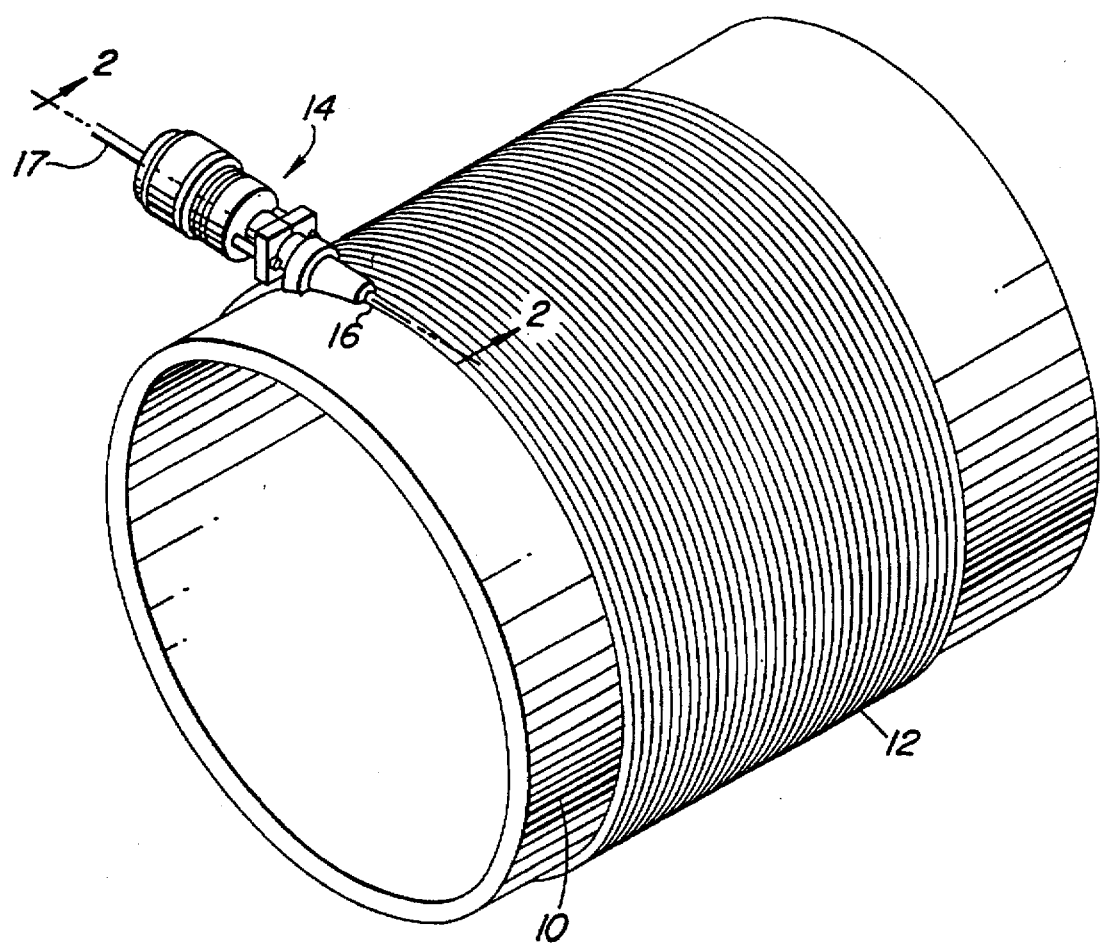
FIG. 1 is a three dimensional view showing a preferred arrangement for the connector of this invention in a preferred application on a mandrel containing a spiral-wound capillary tube.

This connector is specifically suited for a particularly advantageous chromatography arrangement that wraps multiple windings of the fused silica capillary tubing around a mandrel. FIG. 1 shows a typical arrangement of this type having a mandrel 10 with multiple windings of capillary tubing 12. One form of the connector arrangement of this invention communicates an end 16 of capillary tubing 12 with metallic tubing 17. In a preferred form of the invention a tube in the form of a connector body 18 forms an interface between the capillary tube 16 and the metallic tubing 17. The fused silica body will typically have a diameter of from 3 mm to 8 mm. Metallic tubing 17 conducts fluids or solids from the interior of the capillary tubing through connector body 18 to suitable equipment for the collection and analysis of the material recovered from the capillary tubes. Additional details of the spiral wound capillary system can be found in co-pending U.S. Ser. No. 08/394,127, filed on Feb. 24, 1995, the contents of which are hereby incorporated by reference.

Figure 2:
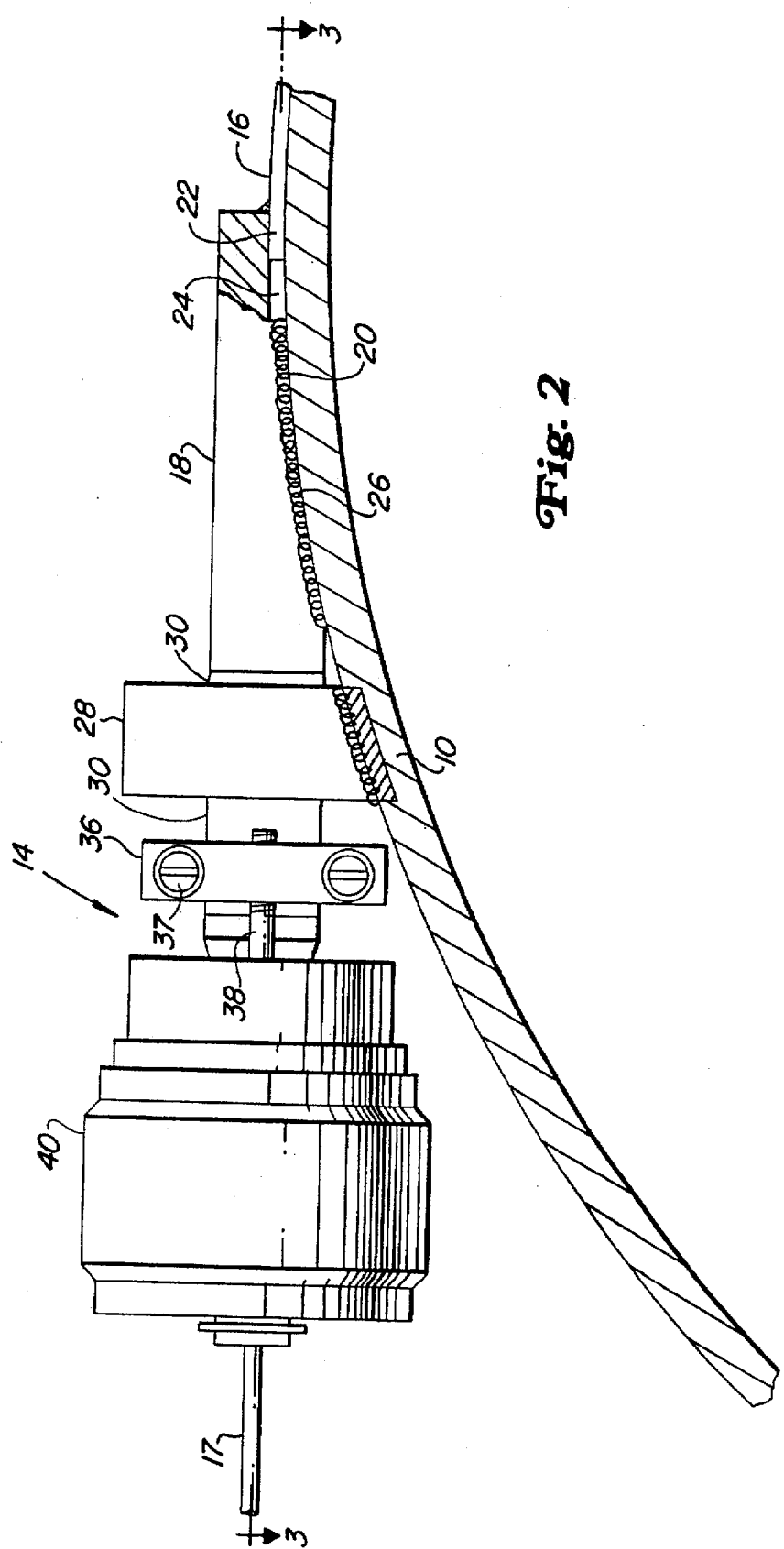
FIG. 2 is a enlarged view of the connector arrangement of this invention taken along lines 2—2.

FIG. 2 shows an enlargement of the connector depicted in FIG. 1 via a view that looks to the side of the mandrel. The connector body 18 is fused to mandrel 10 using any procedure that maintains the integrity of the capillary tubing and securely holds body 18 onto the mandrel. The mandrel 10 typically consists of a silica material similar to the silica body. Lapping the proximate end of the connector body produces a sloped contact surface 20 that conforms to the radius of the mandrel 10. The lapping procedure also removes sufficient material from the connector body to create a longitudinal slot from the central bore of the connector body for receiving the end of capillary tube 16. A cut away view in FIG. 2 depicts the end of connector body 18 showing a longitudinal slot 24 formed by the end of connector body 18 that overlaps end 22 of the capillary tube.

Once the connector body is in place over the mandrel, an oxygen/hydrogen ($H_2/O_2$) micro torch can be used to tack the connector body 18 over the capillary end and onto the mandrel. A bond 26 made of a sol gel material seals the end of the connector body in place over the mandrel and capillary end. The sol gel procedure for sealing interface tube 18 and capillary end 22 to the mandrel uses a sol gel solution consisting of a 50/50 mixture by weight of 200 proof ethyl alcohol and a silica powder containing 0.5 micrometer silica particles. The sol gel mixture undergoes shaking for 5 minutes and ultrasonic treatment for at least 30 minutes before application to the tube surfaces. The sol gel mixture is applied to the mandrel, connector body and capillary tube at ambient temperatures using a thin gauge applicator such as a wire to put droplets of the solid gel mixture over the components. Upon application the sol gel wicks into small spaces between the capillary and silica body. After the applied sol gel mixture has dried thoroughly, slow heating with a micro torch is carried out until the sol gel clarifies and the a sealing bond is completed. The preferred bonding method for bonding of the connector body, mandrel and capillary is further described in copending application U.S. Ser. No. 08/545,492 filed Oct. 19, 1995, the contents of which are hereby incorporated by reference.

Figure 6:
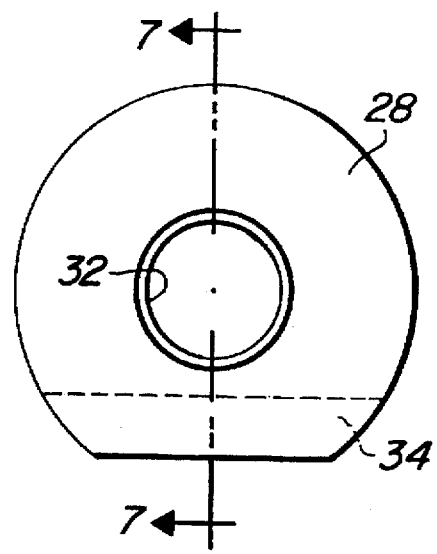
FIG. 6 and 7 depict enlarged views of a clamp for securing the fused silica body to the mandrel.
Figure 7:
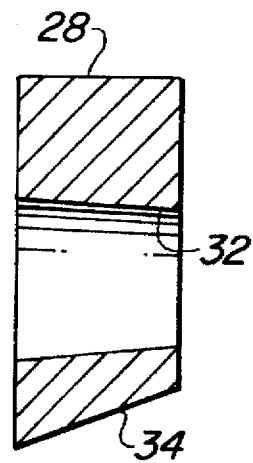
Figure 8:
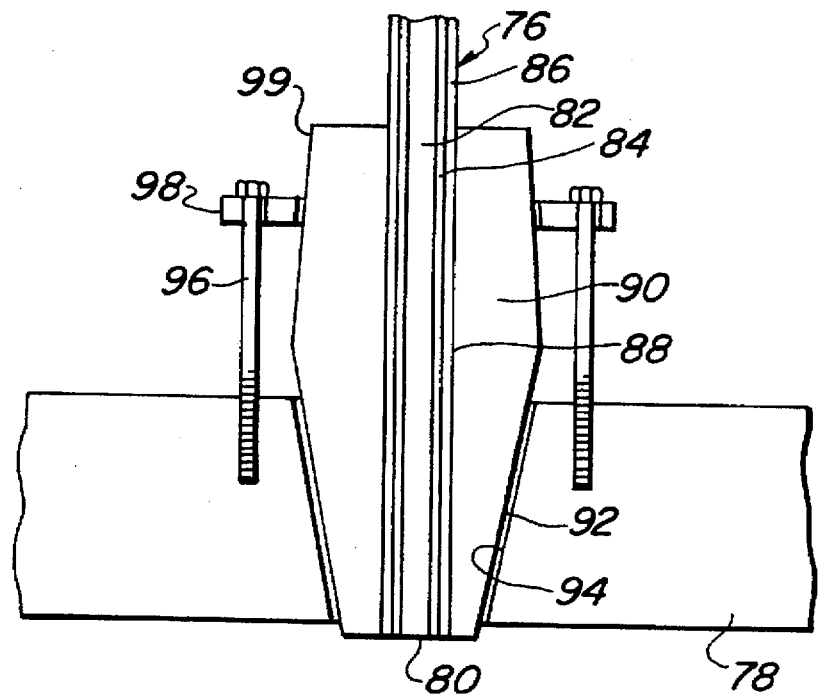
FIG. 8 depicts the connector arrangement of this invention locating an optical wave guide in the wall of cylinder.

A clamp 28 provides further support of the connector body 18 to mandrel 10. Clamp 28 fits over a tapered surface 30 of the interface tube. As shown in FIGS. 6 and 7, clamp 28 has a tapered bore 32 and a beveled surface 34. Beveled surface 34 has an angle corresponding to the tangent of mandrel 18 at the point where clamp 28 contacts the mandrel. Tapered bore 32 surrounds tapered surface 30 and is held in place by fixing the mandrel using the previously described sol gel procedure. Clamp 28 serves primarily to tie connector body to the mandrel close the end of the connector and thereby reduce any bending stresses that may be imposed at the proximate end of the connector body when tightening or loosening the connection. Clamp 28 may be replaced by a solid ligament of fused silica material that is bonded to the silica body and the mandrel.

The remainder of the connector comprising a connector head 40 is secured to connector body 18 by a split ring collar 36 that engages a larger diameter portion of tapered surface 30 and receives a pair of micro bolts 38 that extend into connector head 40. A pair of micro bolts 37 engage the two halves of split ring collar 36 for attachment or removal of the collar from connector body 18.

Figure 3:
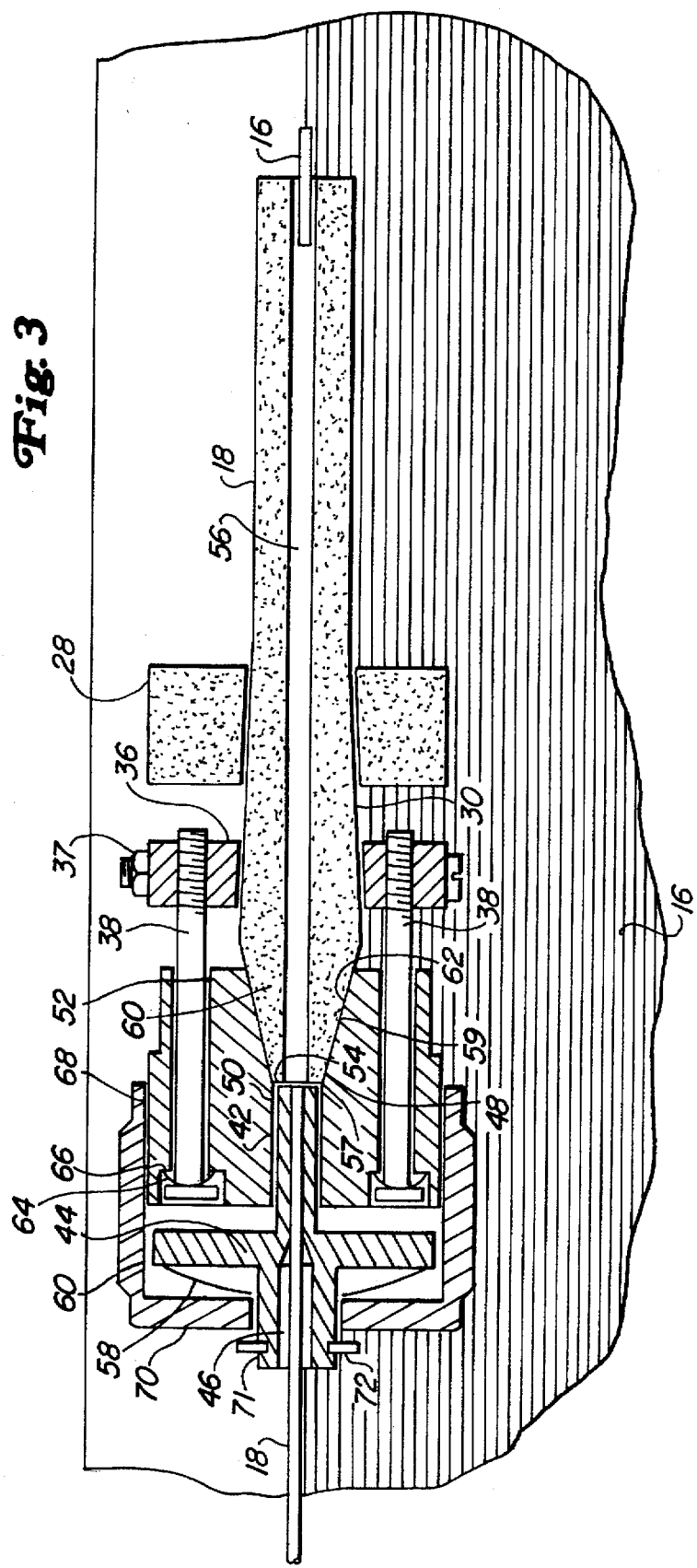
FIG. 3 is a cross-section of the connector shown in FIG. 2 taken along lines 3—3 that also depicts a top section of the mandrel with the capillary robe wound thereon.

Connector head 40 provides the necessary components for sealingly communicating metallic tube 17 with capillary end 22. FIG. 3 shows metallic tube 17 extending into a small diameter bore 42 of a ferrule 44. Small diameter bore 42 sealingly engages the outside of metallic tube 17. Metallic tube 17 passes through an enlarged portion 46 of the ferrule bore which is sized to provide strain relief to the metallic tubing. The distal end of ferrule 44 has a contact face 48 formed orthogonally to bore 42. A bore 50 in an alignment block 52 aligns contact face 48 with a cooperating contact face 54 formed at the distal end of connector body 18. Contact face 54 is formed orthogonally to central bore 56 of connector body 18. In the connector arrangement depicted by FIGS. 1–7, contact faces 48 and 54 provide the primary seal between capillary tube 16 and metallic tube 17. When using the preferred contact face arrangement of this invention, the effectiveness of the primary seal will depend on the orthogonality of the two faces. Preferably, face 54 of the connector body and face 48 of the ferrule will have an orthogonality within less than 0.2 degree and more preferably within less than 0.1 degrees. To further facilitate sealing, the contact faces are lapped to a high surface smoothness of at 6 µm rms or less. The optional use of a gold leaf layer 57 between contact faces 48 and 56 may further enhance the primary seal of the connector. The gold leaf layer requires only a relatively small thickness of about 25 µm. The gold leaf may be placed in the connector by centering it to the face of the fused silica using a pin which passes through the gold into the central bore of the fused silica body. After the gold is centered, the alignment block is slipped over the gold and pushed over the fused silica body forcing the gold to become captive on the face. Removal of the pin follows attachment of the miniature bolts 38 which permanently secures the gold in place.

Sealing pressure for the contact face is provided by a biasing element that act on alignment block 52. One side of a Belleville washer 58 acts against a shoulder 60 of the ferrule 44 to urge contact face 48 against contact face 54. The diameter of contact face 48 and 54 are kept relatively small to maintain high contact pressures with relatively small applied forces. The contact pressure between the two faces will normally exceed 35 kg/cm$^2$. This contact pressure is sufficient to deform the gold leaf when it is present. The typical contact surface will have a diameter of 2 mm or less. The contact face surrounds the central bore of the connector body which typically has a diameter of 250 to 100 µm. For a typical interface tube, these dimensions result in a surface area of about 2 to 3 mm$^2$. Therefore, reasonable axial forces on the order of 1–2 kilograms can generate sufficient pressure to deform the gold leaf and maintain an effective seal.

Bore 50 of alignment block 52 opens divergently to form a frustro conical socket that provides a tapered surface 59 for receiving a distal end 60 of connector body 18. Distal end 60 has a frustro-conical surface 62 that converges in the direction of the contact face 54 to provide a mating contact surface that abuts contact surface 59. Tapered surface 59 confines tapered end 60 to maintain compression on the fused silica material of the connector body. Since the fused silica material has been found to have little tensile strength, maintaining compression about the outer surface of the fused silica material is essential to maintaining the integrity of the sealed connection.

Figure 4:
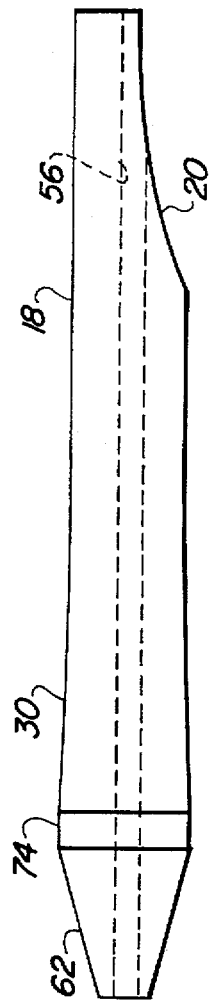
FIGS. 4 and 5 are orthographic projections of a fused silica body that forms a portion of the connector shown in FIGS. 1–3.
Figure 5:
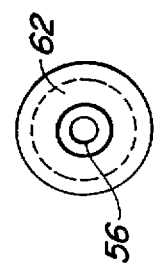

The geometry of the fused silica connector body is a key portion of the preferred embodiment of this invention. FIG. 4 and 5 show the interface tube removed from the connector assembly. Contact surface 20 on the proximate end of the connector body 18 is contoured for contact with the mandrel and intersects the axial bore 56 in the manner previously described. At the other end of the tube a land portion 74 separates section 30 from the convergently tapered contact surface 62. The convergently tapered contact surface 62 borders the contact face 56.

It has been found that the taper angles of the frustoconical surface require a high degree of control to prevent tensile fractures of the fused silica. The convergently tapered surface 62 on the fused silica body and divergently tapered surface 59 on the alignment block will have an included angle of between 20°–40°—with a half angle of the taper preferably falling in a range of 12°–16°. Minimization of stress on the fused silica body is also promoted by maintaining the complementary tapered surfaces between the alignment block and the end of the connector body within a close angular tolerance of less the 0.3 degrees and more preferably less than 0.1 degrees. The surfaces of the tapered surfaces are usually ground to a surface finish in a range of from 1 to 25 µrms. In a further effort to distribute loading across the tapered contact surfaces on the alignment block and connector bodies, these surfaces are preferably ground to a surface finish of about 15 µm rms such that the physical loading between the two surfaces is made on the ridges of the finish to further distribute the loading between the surfaces. Satisfactory tolerance between the taper angles and suitable surface finishes for achieving effective sealing is a function of the relative hardness of the materials. It is anticipated that in most cases the alignment block that directly contacts the fused silica will be a brass material. The above tolerances and finishes are generally suitable for compliant materials such as brass. Where stainless steels and other higher strength materials contact the fused silica surface, tighter tolerances and higher surface finishes may be required.

Micro bolts 38 and an end cap 70 act on alignment block 52 to provide the necessary sealing and containment forces between surfaces. Micro bolts 38 act on clamp 36 which in turn urges distal end 60 of the connector body into alignment block 52 and against face 48 of ferrule 44. The microbolts thereby maintain the compressive loading on contact surfaces 54 and 62. The force supplied by micro bolts 38 must exceed that of belleville washer 58 to prevent the ferrule from pushing surface 62 of connector body end 62 out of contact with the alignment block. Typically, the bolts will produce a net axial force of about 2 kg. The taper between divergent surface 59 of the alignment block and the convergent face 62 of the connector body produces an axial variation in the contact pressure along the surfaces. This contact pressure will usually vary linearly along length of the connector body end 60. The highest stress on the fused silica body will occur near contact face 54 and diminish as the net cross section of the frusto-conical section increases. Compressive loadings in the connector body outside of alignment block 50 are low.

Although the connector may perform adequately without them, the amount of force generated by miniature bolts 38 may be regulated by the use of springs or Belleville washers. FIG. 3 shows a Belleville washer 64 between the head of each bolt 38 and a supporting shoulder 66 of alignment block 52. Tightening bolts 38 to cause a predetermined deflection of Spring 64 will prevent overloading the connector body end 60 and its contact face 62. Collar 36 also serves to distribute the load from miniature bolts 38 about tapered section 30 of the connector body. With respect to end 60 section 30 has a small divergent taper angle that is usually in the range of from about 2°–10° and preferably in the range of 3° to 6°.

Springs and other resilient biasing elements have the advantage of compensating for differences between the low coefficient of expansion associated with the fused silica material and the metallic materials that are typically used for the remainder of the connector. Fused silica will have a coefficient of expansion that is typically ten times less than those associated with most metallic connector elements. The cooperating tapered surfaces can accommodate the relative changes in diameter between the convergently tapered surface of the fused silica and the divergent taper of the receiving element of the fused silica provided the relative angles between the two surfaces are maintained within a suitable tolerance.

Sealing force for ferrule 44 is supplied by end cap 70. A threaded outer portion 68 of alignment block 52 receives a threaded portion of end cap 70. Tightening of end cap 70 over alignment block 52 provides displacement of Belleville washer 58 to load the contact end 48 of ferrule 44 in the manner previously described. An outer portion 71 of ferrule 44 receives a retaining ring 72 that retains end cap 70, belleville washer 58 and ferrule 44 as a unit.

Apart from the fused silica connector body and the clamp 28, the other materials used in the construction of the connector will preferably be made of material suitable for withstanding temperatures of up to 600° C. Brass materials have adequate high temperature properties for collar 36, miniature bolts 38, caps 70, and ferrule 44 to operate at temperature of 600° C. In those applications of the invention where spring elements are used to control forces imposed on the fused silica contact surfaces, high temperature spring material such as Eligiloy are preferred to prevent loss of imposed spring forces as the connector is passed through multiple cycles of high temperature operation.

The figures show a preferred embodiment of this invention which is susceptible to many different arrangements and variations. In essence, the central element of this invention is a fused silica body that can be in the form of an interface tube or a capillary tube. A key feature of the fused silica body is the convergently tapered frustro conical section of the distal end of the body. While useful for controlling forces on the delicate fused silica body, the various spring combinations that interact with miniature bolt and the cap are not essential to the operation of this invention. Suitable compressive forces may be developed to urge the convergently tapered contact face into the alignment block using a direct bolting or clamping arrangements. In addition, a contact face at the end of the fused silica body may be acted upon by an opposing contact face that is again tightened into a sealing arrangement without a deformable biasing element.

Moreover, a key function of the sealing arrangement for this invention is maintaining the integrity of the tapered fused silica contact face. An alternate arrangement for this invention may use an alignment block that contains the tapered surfaces and establishes the primary seal between the tapered contacting surfaces. This type of arrangement would eliminate the orthogonal contact faces and the use of the ferrule. Although shown as a linear surface, effective sealing and confinement may be established by using cooperating curved surfaces as well. Establishing an acceptable seal in such an arrangement would again require a close tolerance between the divergent and convergent surfaces as well as the use of lapping or grinding to provide sufficiently smooth surfaces on both contact faces. An arrangement that eliminates the face seal would further reduce the complexity of the connector arrangement, thereby reducing its bulk and weight.

In order to test the reliability of the seal provided by the connector arrangement, a connector assembly having a configuration that corresponds substantially to that shown in FIGS. 1–3 was tested under vacuum conditions to find its reliability after exposure to several heat and cooling cycles. Each cycle of heating and cooling consisted of raising the temperature of the connection containing the fused silica to a temperature of 600° F. followed by cooling. Throughout this test period, a vacuum of less than 10 μtorr was maintained in the bore that the tubing connects. After 10 cycles of heating and cooling over a period of eight hours, the connection was found to have a leakage rate of less than 10 μtorr.

An alternate application for the connector arrangement of this application shows a glass on glass optical wave guide fiber 76 located in a cylinder wall 78. Fiber 76 has a core 82 surrounding by a cladding 84 which is covered by sheath M. The sheath, cladding and core all extend through a bore 88 of a fused silica body 90 to a detection face 80. Detection face 80 of fiber 76 is directed to the inside of a combustion cylinder to receive detonation spectra from the combustion of hydrocarbon fuels. The outside of sheath 86 of fiber 76 is fused to the inside bore 88 using the previously described silica sol gel bonding technique. The distil end of silica body 90 provides a convergently tapered surface 94. A portion of the cylinder wall 78 acts as the alignment block and provides a divergently tapered surface 92 for receiving tapered surface 94. A pair of micro bolts 96 engage threads in the cylinder wall to urge a sleeve 96 against a tapered surface 99 and supply sealing pressure to tapered surfaces 92 and 94.

The previously mentioned taper angles and preferred tolerances and surfaces finishes are suitable for tapered surfaces 92, 94 and 99.

What is claimed is:

1. A connector arrangement for making connections to fused silica tubing and fibers capable of withstanding temperatures of 600° C. or more said connector comprising:

a fused silica body defining a convergent tapered surface formed on the outside of a distal end of said body, said convergent tapered surface having an included angle of from 20°–40°;

an alignment body comprising a material suitable for withstanding temperatures of up to 600° C. defining a bore forming a divergent tapered surface having substantially the same included angle as said first tapered surface for receiving said distal end of said silica body; and, means for securing said fused silica body to said alignment body and urging said divergent and convergent tapered surfaces into contact.

2. A connector arrangement capable of withstanding temperatures of 600° C. or more for making connections to fused silica tubing said connector comprising:

a fused silica body defining a first bore open to a distal end of said body and a convergent tapered surface formed on the outside of said distal end, said convergent tapered surface having an included angle of from 20° to 40°;

an alignment body comprising a material suitable for withstanding temperatures of up to 600° C. defining a second bore having one end forming a divergent tapered surface having substantially the same included angle as said first tapered surface for receiving said distal end of said silica body; and, means for securing a conduit to said alignment body, communicating said conduit with said first bore and urging said divergent and convergent tapered surfaces into contact.

3. The connector of claim 2 wherein said distal end of said silica body defines a contact face, a sealing body defines a second face, and means are provided for urging said first and second contact faces into sealing contact.

4. The connector of claim 2 wherein said the angle of said divergent tapered surface is within 0.1 degrees of said included angle.

5. The connector of claim 2 wherein a deformable sealing material is located between said tapered surfaces.

6. The connector of claim 5 wherein said deformable material is gold.

7. The connector of claim 2 wherein said convergent tapered surface has a surface finish of 1 to 25 μm rms.

8. The connector of claim 3 wherein contact between said first and second contact surfaces produces a pressure of at least 35 kg/cm².

9. The connector of claim 2 wherein said fused silica tubing has a diameter of less than 7 mm.

10. A connector for capillary tubing defining a capillary bore, said connector comprising:

a fused silica body fixed to said capillary tubing at a proximate end and defining a first bore in communication with said capillary bore; a first trunated conical surface formed on the outside of the silica body at and converging in the direction of the distal end of said silica body and defining a convergent tapered surface having a first included angle of from 20° to 40°;

a first contact face defined by said silica body at the end of said conical surface surrounding an end of said first bore;

an alignment body defining a second bore having one end forming a concave second truncated conical surface defining a divergent tapered surface having a second included angle that differs from said first included angle by less than 0.5 degrees;

a second contact face located in said second bore, having a surface for contacting said first contact face, and defining a central opening; and, means for securing a conduit to said alignment body, communicating said conduit with said central opening and urging said divergent and convergent tapered surfaces and said first and second contact faces into contact.

11. The connector of claim 10 wherein said means for securing said conduit includes a tubing sleeve that defines said second contact face.

12. The connector of claim 10 wherein said the lust included angle is within 0.1 degrees said second included angle.

13. The connector of claim 10 wherein a deformable sealing material is located between said tapered surfaces.

14. The connector of claim 10 wherein said first and second conical surfaces have a surface finish of from 1 to 25 μm rms.

15. The connector of claim 10 wherein contact between said first and second contact surfaces produces a pressure of at least 35 kg/cm².

16. The connector of claim 10 wherein said fused silica body has a diameter of less than 8 mm.

17. The connector of claim 10 wherein a sleeve extends into said second bore and defines said second contact face to provide said means for communicating said conduit with said first bore.

18. The connector of claim 17 wherein said sleeve defines a shoulder and a threaded cap engages said shoulder and said sleeve to provide said means for urging said fast and contact faces into contact.

19. The connector of claim 10 wherein a collar is fixed to said silica body and at least a pair of draw bolts engage said collar and said alignment body to provide said means for urging said divergent and convergent tapered surfaces into contact.

20. The connector of claim 10 wherein said silica body defines an intermediate tapered surface diverging in the direction of said distil end, a sleeve having a coincident tapered surface that engages said intermediate surface and a ligament engaging said alignment block to urge said divergent and convergent tapered surfaces into contact.

21. A fused silica connector arrangement for joining capillary tubing to metallic tubing, said connector arrangement comprising:

a fused silica body fixed to said capillary tubing at a proximate end and defining a transverse first bore in communication with a capillary bore of said capillary tubing, the distal end of said body having outer diverging and converging frusto-conical surfaces defining an enlarged distal end with said converging frusto-conical surface having an included angle of from 20° to 40°;

a first contact face at the distil end of said body formed by the small end of said convergent frusto-conical surface, said contact face extending perpendicular to said first bore and having a central portion defining an opening for said first bore;

an alignment body defining a cylindrical second bore having one end forming a concave truncated conical surface for receiving said distal end of said body, said concave truncated conical surface defining a second included angle that differs from said fast included angle by less than 0.1 degrees;

a collar surrounding said diverging frusto conical-surface with a coincident tapered surface;

at least one bolt extending into said alignment block and collar for urging said distil end of said body against said concave truncated surface;

a ferrule having a cylindrical end adapted to extend into said second bore and defining a transverse third bore aligned with said fast bore and means for retaining metallic tubing, said cylindrical end deeming a second contact face at the proximate end of said ferrule adapted for sealing contact with said first contact face; and, a cap that engages said alignment block and ferrule to urge said first and second contact faces into contact.

22. The connector of claim 21 wherein said ferrule defines a shoulder and a spring is disposed between said cap and said shoulder to control the pressure between said fast and second contact faces.

23. The connector of claim 22 wherein said bolt acts against a spring to urge body against said concave truncated surface.

24. The connector of claim 23 wherein said fused silica body and said capillary tubing are fixed to a mandrel that supports spiral windings of said tubing.

* * * * *